(12) United States Patent
Kobayashi (10) Patent No.: US 7,699,967 B2
(45) Date of Patent: Apr. 20, 2010

(54) ANALYSIS IMPLEMENT WITH OPENING IN INSULATION FILM (75) Inventor: Taizo Kobayashi, Kyoto (JP)

(73) Assignee: Arkray, Inc., Kyoto (JP)

(*) Notice: Subject to any disclaimer, the term of this patent is extended or adjusted under 35 U.S.C. 154(b) by 1106 days.

(21) Appl. No.: 10/560,015

(22) PCT Filed: Jun. 15, 2004

(86) PCT No.: PCT/JP2004/008348

§ 371 (c)(1),
(2), (4) Date: Dec. 8, 2005

(87) PCT Pub. No.: WO2004/113903

PCT Pub. Date: Dec. 29, 2004

(65) Prior Publication Data

US 2006/0131171 A1 Jun. 22, 2006

(30) Foreign Application Priority Data

Jun. 19, 2003 (JP) ............................. 2003-175248

(51) Int. Cl.
C12Q 1/00 (2006.01)
(52) U.S. Cl. ..................... 204/403.14; 204/403.02; 204/403.03; 205/777.5; 205/792
(58) Field of Classification Search .................. 204/403.01–403.15; 205/777.5–778, 792
See application file for complete search history.

(56) References Cited

U.S. PATENT DOCUMENTS

| 5,120,420 A | * | 6/1992 | Nankai et al. ........ 204/403.11 |
| 5,320,732 A | | 6/1994 | Nankai et al. |
| 5,582,697 A | | 12/1996 | Ikeda et al. |
| 5,985,116 A | | 11/1999 | Ikeda et al. |
| 6,719,923 B2 | | 4/2004 | Stiene et al. |
| 6,743,635 B2 | * | 6/2004 | Neel et al. ................ 436/95 |
| 6,946,299 B2 | * | 9/2005 | Neel et al. ................ 436/95 |
| 7,047,795 B2 | * | 5/2006 | Sato .......................... 73/64.56 |
| 2001/0042683 A1 | * | 11/2001 | Musho et al. .............. 204/403 |
| 2003/0125403 A1 | | 7/2003 | Steine et al. |

FOREIGN PATENT DOCUMENTS

| JP | 8-10208 | | 1/1996 |
| JP | 8-320304 | | 3/1996 |
| JP | 10-185860 | | 7/1998 |
| JP | 2002-181758 | | 6/2002 |
| WO | WO 02/32559 | | 4/2002 |
| WO | WO0232559 | * | 4/2002 |
| WO | WO03012421 | * | 2/2003 |

* cited by examiner

Primary Examiner—Nam X Nguyen
Assistant Examiner—Bach T Dinh
(74) Attorney, Agent, or Firm—Hamre, Schumann, Mueller & Larson, P.C.

(57) ABSTRACT

The present invention relates to an analytical tool (X) which includes a substrate (1), a flow path for moving a sample along the substrate (1), a reagent portion (14) provided in the flow path, and an insulating film (13) covering the substrate (1) and including an opening (15a) for defining a region for forming the reagent portion (14). The insulating film (13) further includes at least one additional opening (15b) positioned in a longitudinal direction (N1) relative to the opening (15a). For instance, the flow path is configured to move the sample by capillary force.

11 Claims, 13 Drawing Sheets

ANALYSIS IMPLEMENT WITH OPENING IN INSULATION FILM

TECHNICAL FIELD

The present invention relates to an analytical tool used for analyzing a particular component (such as glucose, cholesterol or lactic acid) contained in a sample (e.g. biochemical sample such as blood or urine).

BACKGROUND ART

Figure 9:
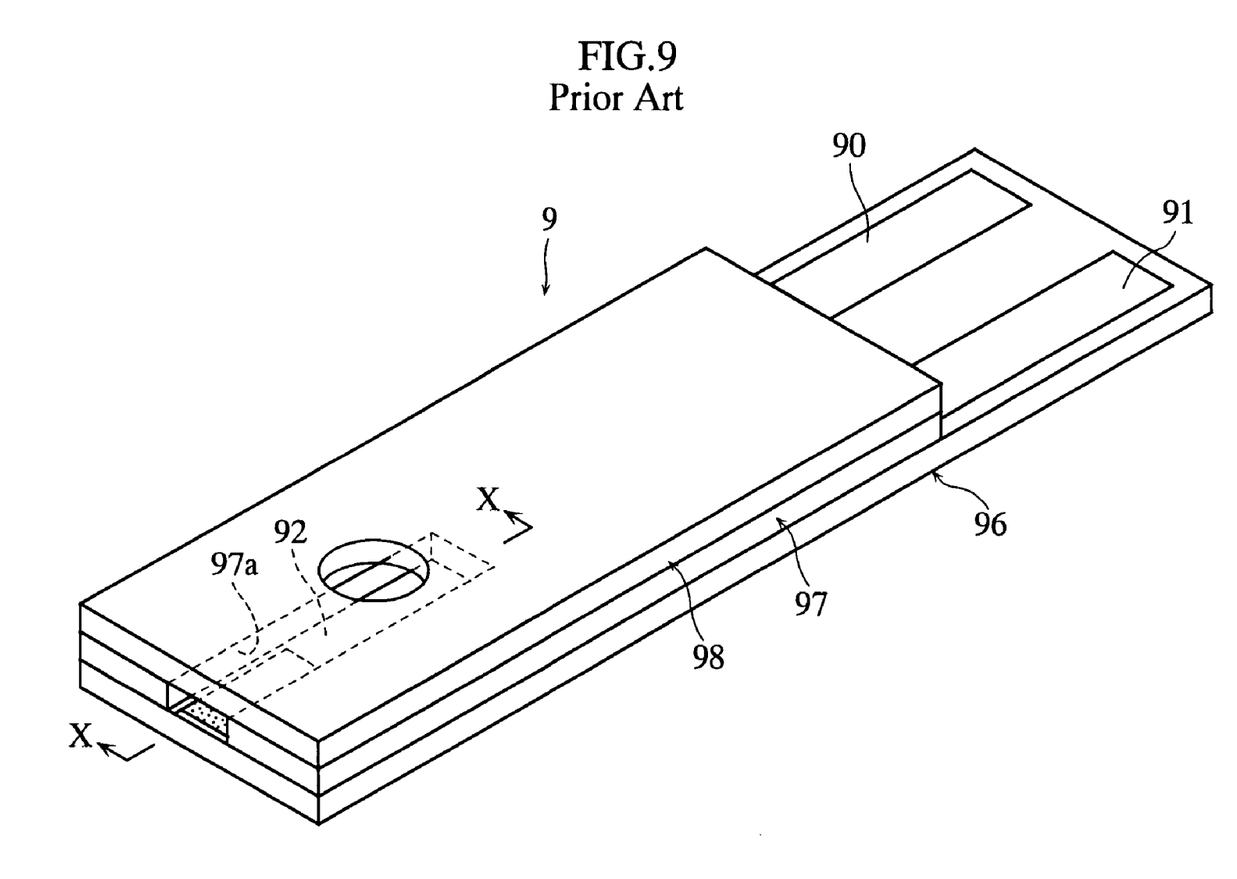
FIG. 9 is an overall perspective view showing a prior art glucose sensor.
Figure 10:
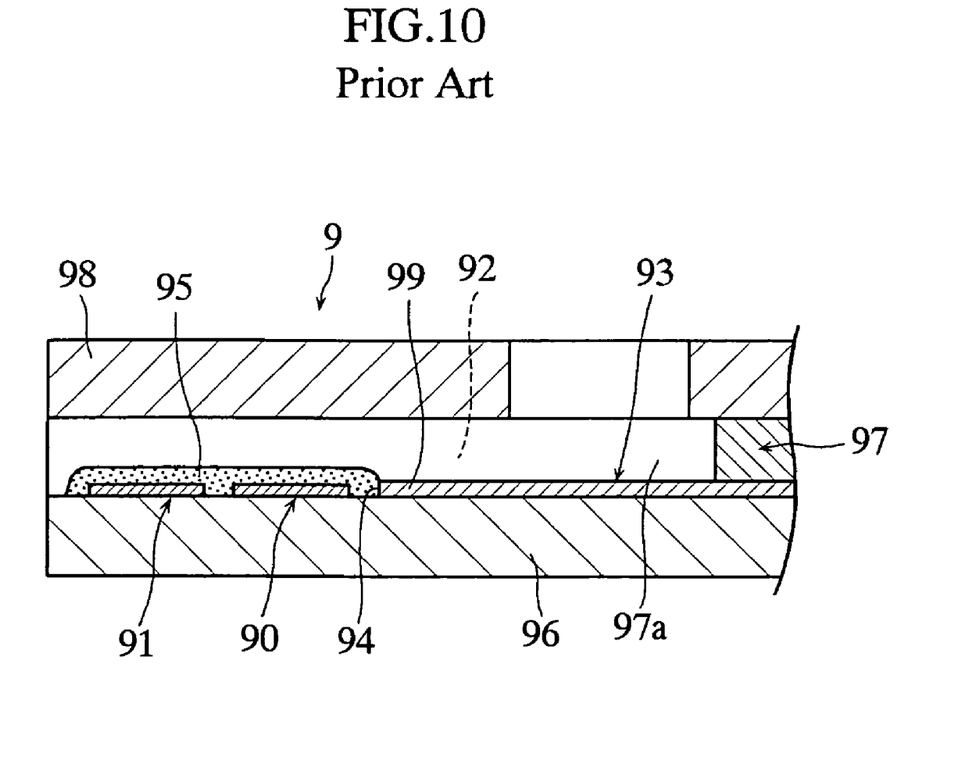
FIG. 10 is a sectional view taken along lines X-X in FIG. 9.
Figure 11:
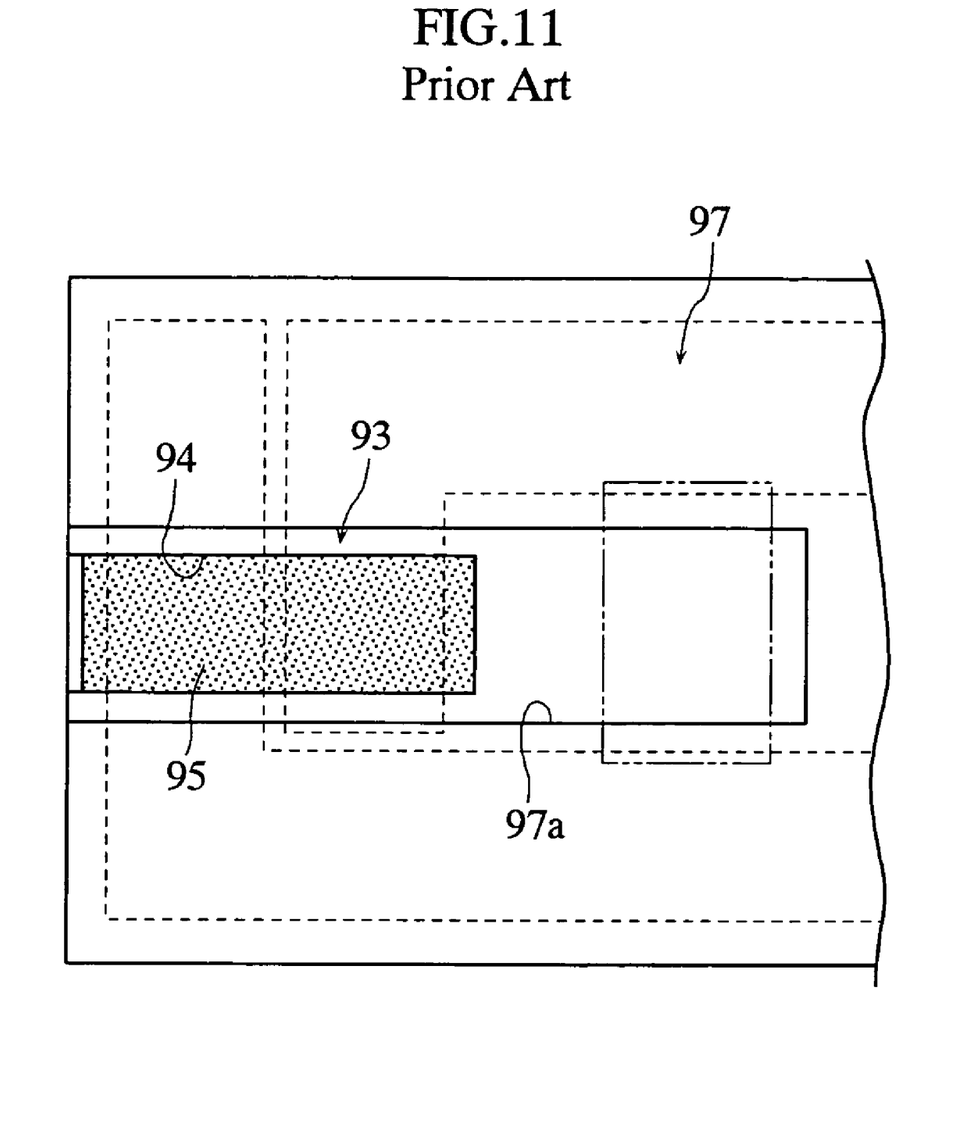
FIG. 11 is a plan view showing an end of the glucose sensor of FIG. 9 in a state in which the cover and the spacer are removed.

To measure a glucose level in blood, a method which utilizes a disposable biosensor is often employed as an easy method of measurement (See Patent Document 1, for example). Like the glucose sensor 9 shown in FIGS. 9 and 10 of the present application, there exists a glucose sensor configured to measure the response current necessary for the computation of a blood glucose level by using a working electrode 90 and a counter electrode 91. In the glucose sensor 9, blood is moved by a capillary force generated in the capillary 92, and the amount of electron transfer upon the reaction between blood and a reagent is measured as the response current. As shown in FIGS. 10 and 11, the reagent is retained as a reagent portion 95 in an opening 94 of an insulating film 93 on a substrate 96. The reagent portion 95 is formed to be highly soluble so that the reagent is dispersed in blood when blood is introduced. As shown in FIGS. 9 and 10, the capillary 92 is defined by stacking a cover 98 to the substrate 96 via a spacer 97 formed with a slit 97a.

Figure 12A:
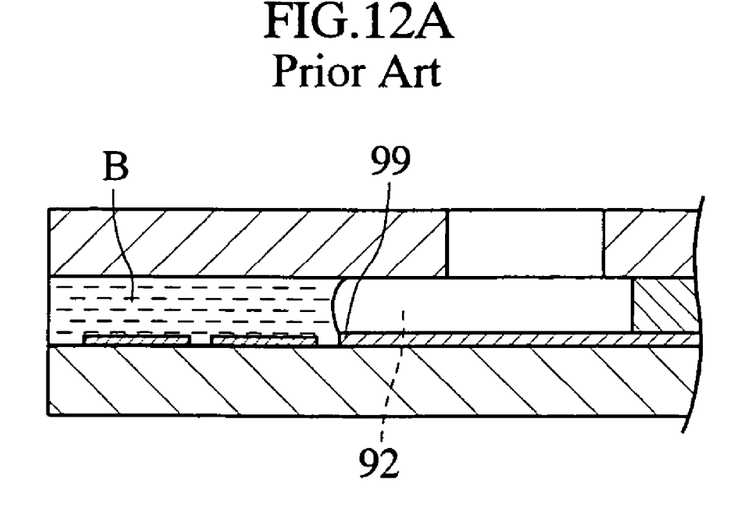
Figure 12B:
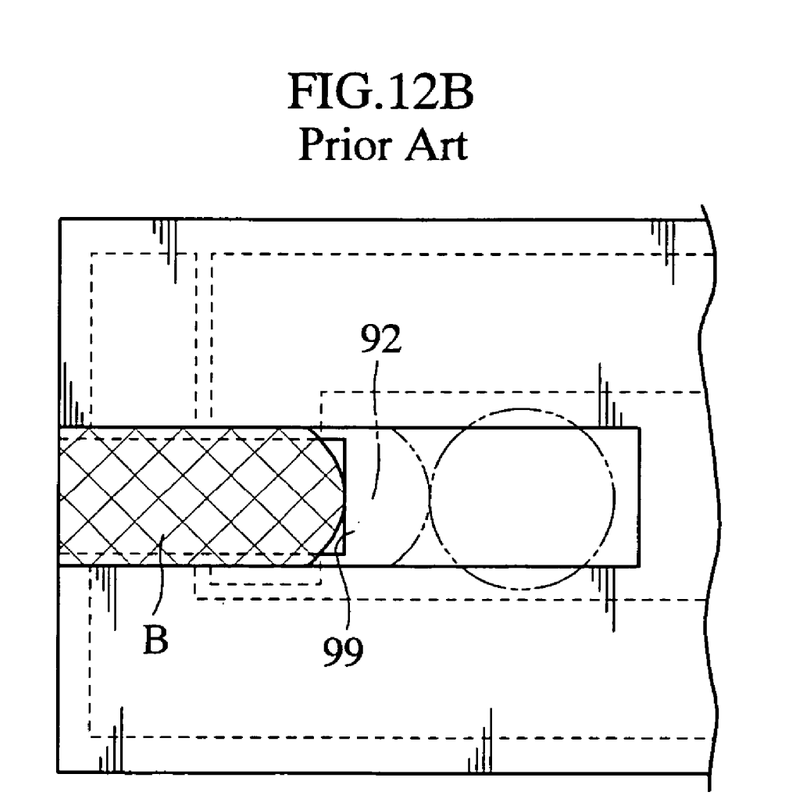
FIG. 12B is a sectional view corresponding to FIG. 11.

The speed of movement of blood (suction force acting on blood) in the capillary 98 depends on the wettability of a surface of the cover 98 and the solubility of the reagent portion 95. Generally, the wettability of the cover 98 and the solubility of the reagent portion 95 deteriorate with time or depending on the temperature. As better shown in FIG. 10, on the surface of the substrate 96, a stepped portion 99 is formed due to the provision of the opening 94 in the insulating film 93. Therefore, as shown in FIGS. 12A and 12B, the blood B introduced into the capillary 92 may be stopped at the stepped portion 99 in moving the capillary 92. Such a phenomenon is more likely to occur as the suction force in the capillary 92 deteriorates, i.e., as the wettability of the cover 98 and the solubility of the reagent portion 95 deteriorate.

Figure 13:
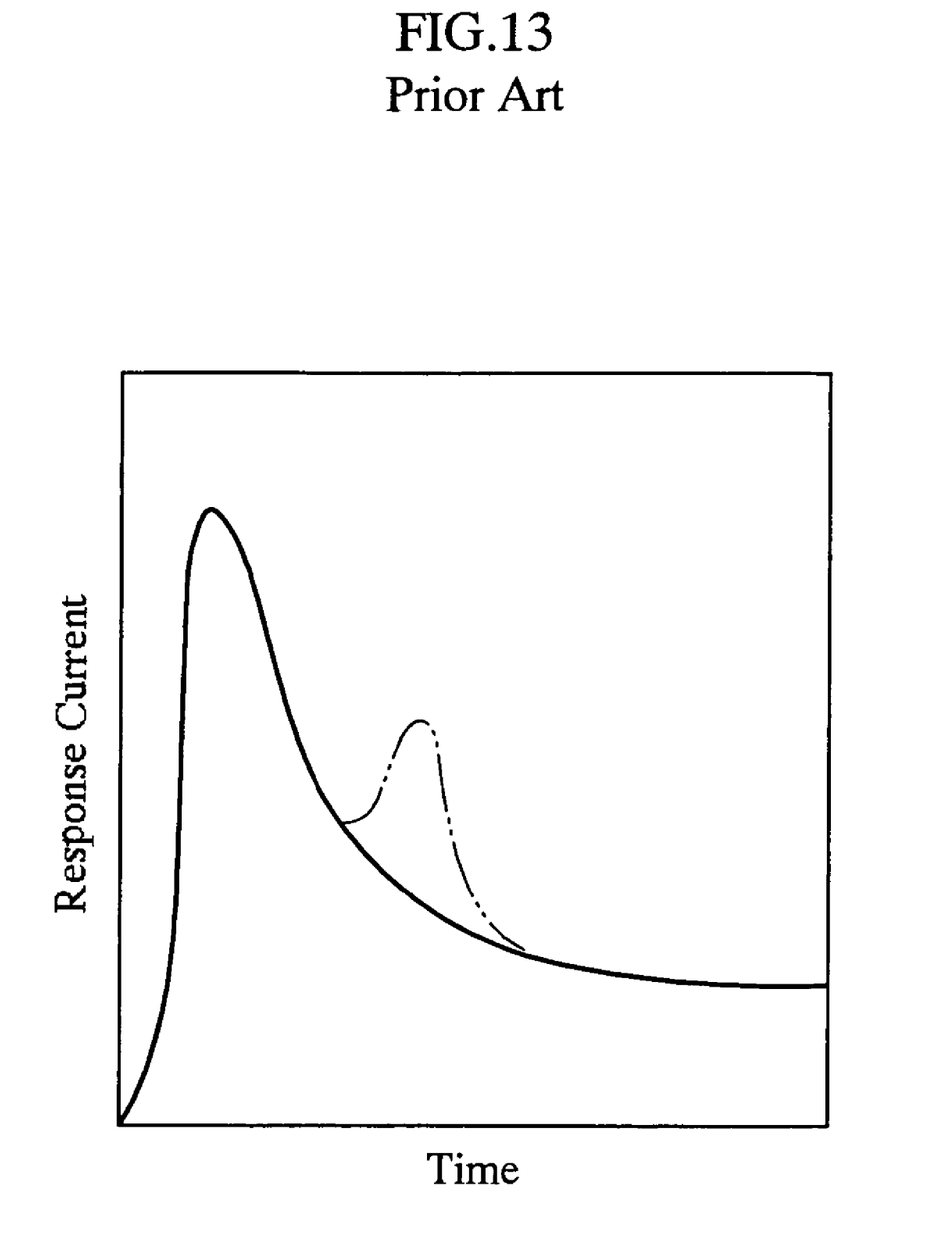
FIG. 13 is a graph showing an example of change of responsive current with time, which is measured in the prior art glucose sensor.

The blood B which has stopped moving at the stepped portion 99 may stop its progress in that state. In some cases, however, the blood B moves again gradually and then suddenly moves largely. When the blood B moves again, the amount (concentration) of electron mediator existing around the working electrode 90 and the counter electrode 91 suddenly changes. In such a case, as indicated by phantom lines in FIG. 13, the measured response current suddenly increases. The phenomenon that the blood B moves again does not necessarily occur at each time of blood glucose level measurement, and the timing at which the blood movement phenomenon occurs is not constant in glucose sensors 9. Therefore, the glucose sensor 9 in which the blood B may move again has poor reproducibility of current measurements, and hence has poor reproducibility of blood glucose levels obtained by computation.

Patent Document 1: JP-A 8-10208

DISCLOSURE OF THE INVENTION

An object of the present invention is to provide an analytical tool with a flow path for moving a sample, which is capable of stably supplying the sample for a long period of time and enhancing the reproducibility of sample analysis.

An analytical tool provided according to the present invention comprises a substrate, a flow path for moving a sample along the substrate, a reagent portion provided in the flow path, and an insulating film covering the substrate and including an opening for defining a region for forming the reagent portion. The insulating film further includes at least one additional opening positioned downstream from the opening in a movement direction in which the sample moves.

For instance, the flow path is configured to move the sample by capillary force.

For instance, the analytical tool of the present invention may be adapted to use a biochemical sample (such as blood, urine or saliva) as the sample.

The analytical tool of the present invention may further comprise a first and a second electrodes provided at the substrate. In this case, the insulating film covers the first and the second electrodes, with part of the first and the second electrodes exposed.

For instance, at least one additional opening is connected to the opening. In this case, the insulating film includes a control edge defining a downstream edge of the region for forming the reagent portion in the movement direction.

For instance, at least one additional opening is connected to the opening at a portion of the control edge adjoining in a direction which is perpendicular to the movement direction.

The control edge may be in the form of a straight line extending in a direction which is perpendicular to the movement direction. In this case, the dimension of the control edge in the perpendicular direction is set to 60 to 95% of the dimension of the opening in the perpendicular direction. The control edge may be in the form of a curved line dented toward a downstream side in the movement direction.

For instance, the insulating film includes an island portion which is in the form of an island and which includes the control edge. The island portion may have a width which decreases as the island portion extends downstream in the movement direction. The configuration of the island portion may be triangular or semicircular, for example.

Alternatively, the insulating film may include a peninsula portion which is in the form of peninsula and which includes the control edge. In this case, at least one additional opening includes a pair of additional openings arranged to adjoin the peninsula portion in a width direction. Each of the paired openings may have a constant width. Alternatively, each of the paired openings includes a narrow portion positioned relatively upstream in the movement direction and a wide portion positioned downstream from the narrow portion.

At least part of at least one additional opening may be offset relative to the opening in the perpendicular direction.

For instance, the flow path may be formed by stacking a cover to the substrate via a spacer. The spacer includes a pair of surfaces defining the dimension of the flow path in the perpendicular direction and facing each other while being spaced from each other in the perpendicular direction. In this case, the spacing between the paired facing surfaces is larger than the dimension of the opening in the perpendicular direction.

When the flow path is configured to move the sample by capillary force, the cover includes a discharge port for discharging gas from within the flow path. In this case, the downstream end of the opening in the movement direction is positioned upstream from the upstream end of the discharge port in the movement direction.

BRIEF DESCRIPTION OF THE DRAWINGS

FIG. 12 includes views for describing problems of the prior art glucose sensor, and FIG. 12A is a sectional view corresponding to FIG. 10, whereas

BEST MODE FOR CARRYING OUT THE INVENTION

Figure 1:
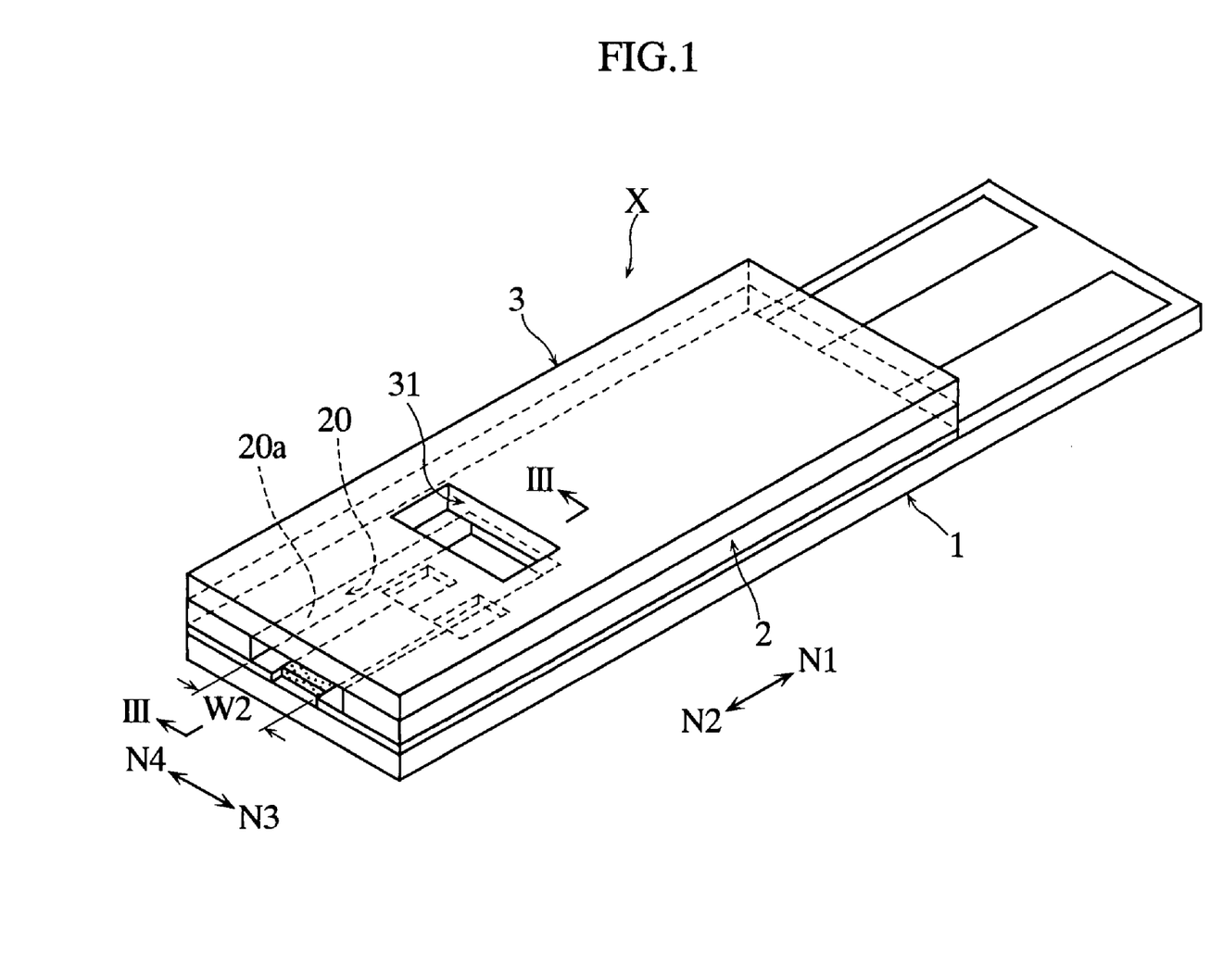
FIG. 1 is an overall perspective view of an example of glucose sensor according to the present invention.
Figure 2:
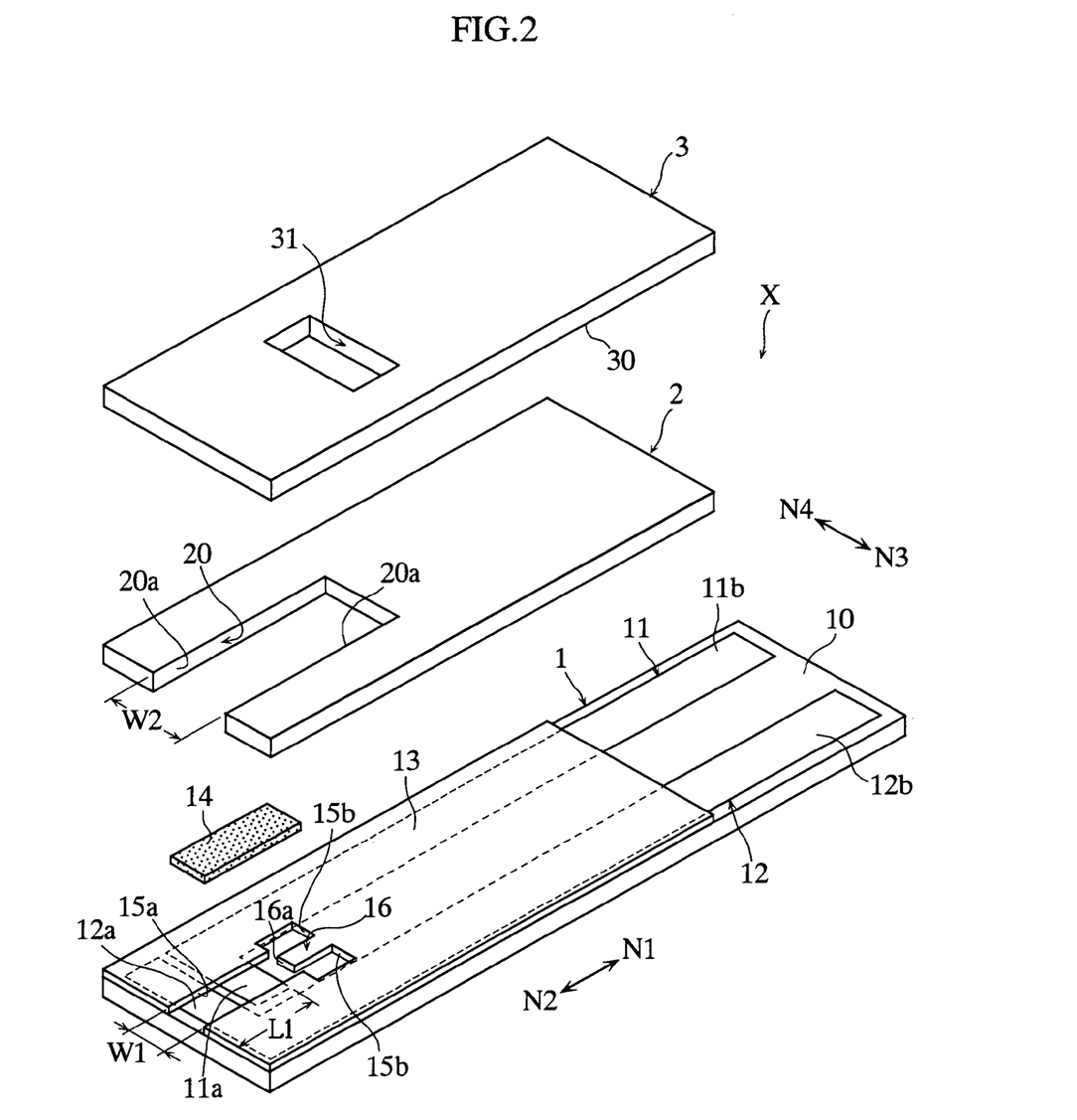
FIG. 2 is an exploded perspective view of the glucose sensor shown in FIG. 1
Figure 3:
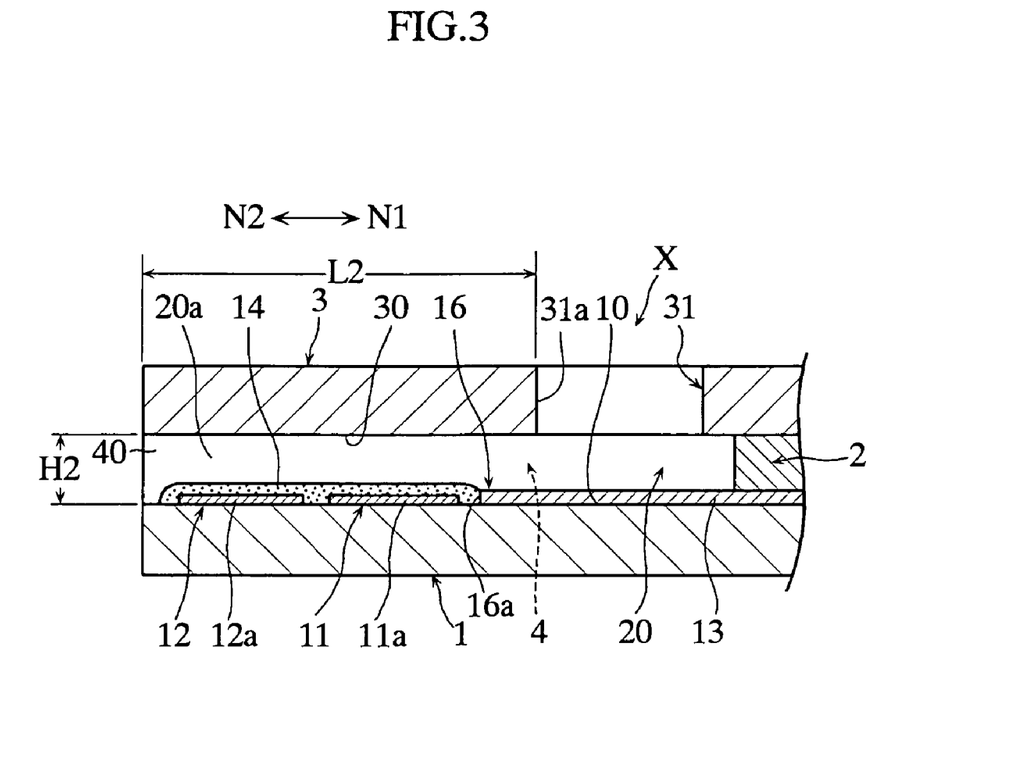
FIG. 3 is a sectional view taken along lines III-III in FIG. 1.

The glucose sensor X shown in FIGS. 1 through 3 is a disposable sensor which is mounted, in use, to a concentration measuring apparatus (not shown) to measure a blood glucose level. The glucose sensor X comprises a substrate 1 having an elongated rectangular configuration, and a cover 3 stacked to the substrate via a spacer 2. In the glucose sensor X, these elements 1-3 define a capillary 4 extending in the longitudinal direction of the substrate 1. The capillary 4 serves to move the blood introduced through an introduction port 40 in the longitudinal direction of the substrate 1 (the direction of N1 in figures) by utilizing capillary action and serves to retain the introduced blood.

The spacer 2 defines the distance from the upper surface 10 of the substrate 1 to the lower surface 30 of the cover 3, i.e. the height of the capillary 4, and may comprise a double-sided tape, for example. The spacer 2 includes a slit 20 having an open front end. The slit 20 defines the width of the capillary 4, and the open front end of the slit 20 provides the introduction port 40 for introducing blood into the capillary 4. The slit 20 includes a pair of facing surfaces 20a facing each other while being spaced from each other in the widthwise direction (N3, N4) of the substrate 1.

The cover 3 includes a through-hole 31. The through-hole 31 is utilized for discharging gas from within the capillary 4 to the outside. The surface of the cover 3 which faces the capillary 4 is made hydrophilic. Such a cover 3 may be provided by forming the entirety of the cover 3 by using a material having a high wettability such as vinylon or high crystallinity PVA or hydrophilically treating the surface of the cover which faces the capillary 4. For example, the hydrophilization may be performed by the irradiation of ultraviolet rays or the application of a surfactant such as lecithin.

As clearly shown in FIGS. 2 and 3, the substrate 1 is made of resin such as PET. The upper surface 10 of the substrate is formed with a working electrode 11, a counter electrode 12, an insulating film 13 and a reagent portion 14. Most part of the working electrode 11 and the counter electrode 12 extend in the longitudinal direction of the substrate 1 (the direction of N1, N2 in the figures), but the ends 11a and 12a thereof extend in the widthwise direction of the substrate 1 (the direction of N3, N4 in the figures). The working electrode 11 and the counter electrode 12 further include ends 11b and 12b constituting terminals for coming into contact with terminals-provided in the concentration measuring apparatus (not shown). The working electrode 11 and the counter electrode 12 may be made by screen printing using conductive carbon ink.

The insulating film 13 serves to protect the working electrode 11 and the counter electrode 12 from water and dust, for example. The insulating film 13 is made hydrophobic as compared with the surface of the substrate 1, the working electrode 11 and the counter electrode 12, and the contact angle at the surfaces is set to 100 to 120 degrees, for example. Such an insulating film 13 may be provided by applying ink containing a water repellent material and then drying, or by curing UV curing resin containing a water repellent agent. As better shown in FIGS. 2 and 4, the insulating film 13 covers most part of the working electrode 11 and counter electrode 12, while leaving the ends 11a, 12a, 11b and 12b of the working electrode 11 and the counter electrode 12 exposed. The insulating film 13 includes a first opening 15a and a pair of second openings 15b.

Figure 4:
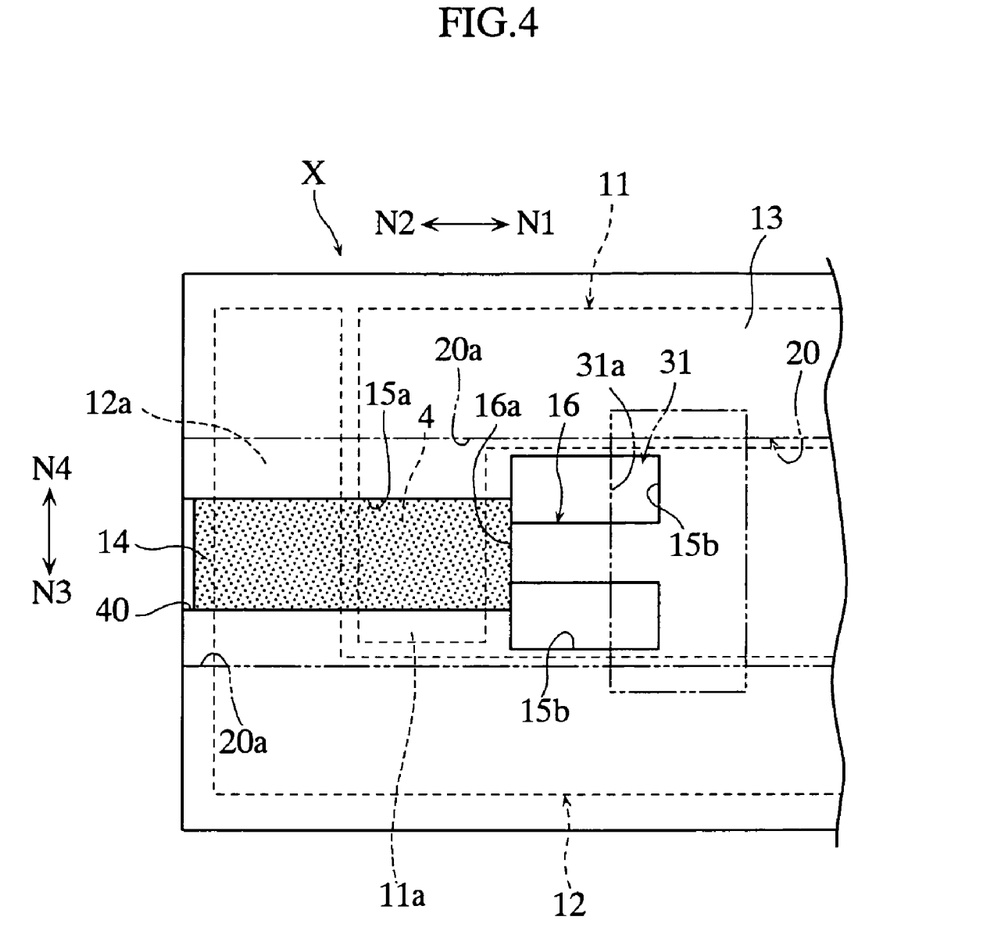
FIG. 4 is a plan view showing an end of the glucose sensor of FIG. 1 in a state in which the cover and the spacer are removed.

The first opening 15a defines a region for forming the reagent portion 14 on a portion of the substrate 1 at which the ends 11a and 12a of the working electrode 11 and the counter electrode 12 are formed. The first opening 15a has an elongated rectangular configuration extending in the longitudinal direction of the substrate 1 (the direction of N1, N2 in the figures), and has a width W1 which is smaller than the distance W2 between the facing surfaces 20a of the slit 20 of the spacer 2.

The paired second openings 15b serve to promote the movement of blood beyond the first opening 15a in the capillary 4A. The second openings 15b are rectangular, spaced from each other in the widthwise direction of the substrate 1, and arranged on the N1 direction side of the first opening 15a (downstream in the direction of movement of blood in the capillary 4). Each of the second openings 15b is connected to the first opening 15a and includes a portion which is offset from the first opening 15a in the widthwise direction of the substrate 1 (the direction of N3, N4 in figures). Between the second openings 15b is provided a stopper portion 16. The stopper portion 16 comprises part of the insulating film 13 and is shaped like a peninsula. The stopper portion 16 includes an edge 16a at opposite sides of which the second openings 15b are connected to the first opening 15a. As a result, the dimension of each second opening 15b in the direction of N3, N4 is larger than the dimension of the connecting portion between the first opening 15a and the second opening 15b in the direction of N3, N4.

As will be described later in detail, in forming the reagent portion 14 in the first opening 15a, the stopper portion 16 serves to prevent the reagent solution to form the reagent portion 14 from spreading more than necessary in the direction of N1. Specifically, this role is substantially fulfilled by the control edge 16a. The control edge 16a defines the boundary between the first opening 15a and the stopper portion 16 and is positioned closer to the introduction port 40 (on the N2 direction side) than the edge 31a of the through-hole 31 of the cover 3 is. For instance, the dimension, i.e., the length of the control edge 16a is set to 60 to 95% of the dimension of the first opening 15a in the widthwise direction (the direction of N3, N4 in the figures). When the dimension of the control edge 16a is unfavorably smaller than the dimension of the first opening 15a in the direction of N3, N4, the spreading of the reagent solution in the direction of N1 cannot be sufficiently suppressed, so that the reagent solution flows into the second openings 15b. On the other hand, when the difference between the dimension of the control edge 16a and that of the first opening 15a in the direction of N3, N4 is unfavorably small, the blood introduced into the capillary 4 cannot be sufficiently moved into the second openings 15b.

The reagent portion 14 is provided in the first opening 15a of the insulating film 13 so as to bridge the ends 11a and 12a of the working electrode 11 and the counter electrode 12. For instance, the reagent portion includes an electron mediator, and a relatively small amount of oxidoreductase. The reagent portion 14 is in a porous solid state easily soluble in blood. Therefore, when blood is introduced into the capillary 4, blood easily moves along the surface of the substrate 1 due to the action of the reagent portion 14, and a liquid phase reaction system including the electron mediator, oxidoreductase and glucose is established in the capillary 4.

As the oxidoreductase, use may be made of GOD or GDH, and typically, PQQGDH may be used. As the electron mediator, use may be made of ruthenium complexes or iron complexes, and typically $[Ru(NH_3)_6]Cl_3$ or $K_3[Fe(CN)_6]$ may be used.

For instance, the reagent portion 14 may be formed by dispensing a reagent solution containing electron mediator and oxidoreductase into the opening 15a and then drying the reagent solution. When a reagent solution is dispensed into the first opening 15a, the reagent solution tries to spread in the first opening 15a. However, the spreading is stopped at a pair of edges of the first opening 15a which are opposite in the widthwise direction of the substrate 1 (the direction of N3, N4 in the figures) and the edge 16a of the stopper portion 16. Therefore, the reagent solution can be dispensed selectively into the first opening 15a, and the reagent portion 14 can be formed selectively in the first opening 15a.

A method for measuring a glucose level by using the glucose sensor X will be described.

With the glucose sensor X, the measurement of a blood glucose level can be performed automatically by mounting the glucose sensor X to a concentration measuring apparatus (not shown) and introducing blood into the capillary 4 through the introduction port 40 of the glucose sensor X.

When the glucose sensor X is mounted to a concentration measuring apparatus (not shown), the working electrode 11 and the counter electrode 12 of the glucose sensor X come into contact with terminals (not shown) of the concentration measuring apparatus. When blood is introduced into the capillary 4, the blood moves from the introduction port 40 toward the through-hole 31 due to the capillary action occurring in the capillary 4. As the blood moves, the reagent portion is dissolved by the blood, whereby a liquid phase reaction system is established in the capillary 4. By using the working electrode 11 and the counter electrode 12, a voltage can be applied to the liquid phase reaction system or the response current when a voltage is applied can be measured.

In the liquid phase reaction system, the oxidoreductase, for example, reacts specifically with glucose in blood to remove electrons from glucose, and the electrons are supplied to the electron mediator to make the electron mediator a reduction type. When a voltage is applied to the liquid phase reaction system by using the working electrode 11 and the counter electrode 12, electrons are supplied from the electron mediator, which has become the reduction type, to the working electrode 11. Therefore, in the concentration measuring apparatus, the amount of electrons supplied to the working electrode 11 can be measured as the response current. In the concentration measuring apparatus (not shown), the blood glucose level is computed based on the response current measured when a predetermined time has elapsed from the introduction of blood into the capillary 4.

In the glucose sensor X, the first opening 15a and the second openings 15b of the insulating film 13 are connected to each other. Therefore, on the surface of the substrate 1 within the capillary 4, the portion which is not covered by the insulating film 13, i.e., the portion which is more hydrophilic than the insulating film 13 extends in the movement direction N1 of blood. Since blood can positively move through the hydrophilic region in the glucose sensor X, blood positively moves from the first opening 15a toward the second openings 15b. Moreover, since the width of each second opening 15b is larger than the dimension of the connecting portion between the first opening 15a and the second opening 15b, the movement of blood from the first opening 15a to the second opening 15b is further facilitated. As a result, it is possible to prevent blood from once stopping at the edge of the first opening 15a, i.e. at the edge 16a of the stopper portion 16 and then moving again. Accordingly, the possibility that the amount (concentration) of the electron mediator existing around the end 11a of the working electrode 11 suddenly changes is reduced, so that the response current measurement becomes close to the value which should be obtained. Therefore, in the glucose sensor X, the reproducibility of response current measurement, and hence the reproducibility of the blood glucose level obtained by computation can be enhanced. Such an advantageous is obtained when the wettability (hydrophilic property) of the cover 3 or the solubility of the reagent portion 14 is reduced with time or depending on the temperature and hence the suction force in the capillary 4 is deteriorated.

Figure 5A:
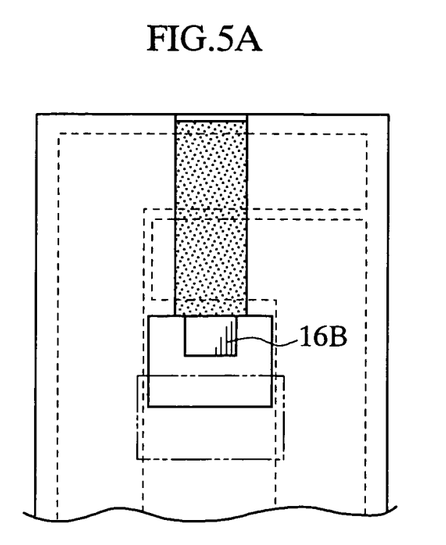
FIG. 5 includes plan views corresponding to FIG. 4, showing other examples of stopper portion of the glucose sensor.
Figure 5B:
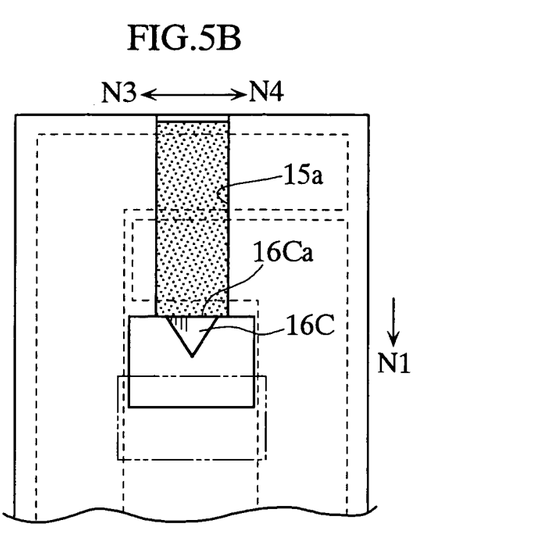
Figure 5C:
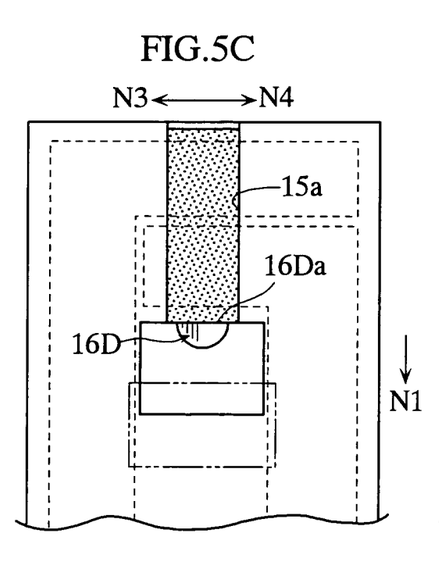

The present invention is not limited to the foregoing embodiment but may be modified in various ways. For instance, as shown in FIG. 5A, the stopper portion 16B may be in the form of a rectangular island which is separate from the insulating film 13. In the case where a stopper portion which is separate from the insulating film is provided, the configuration may not be rectangular but may be triangular or semicircular like the stopper portions 16C, 16D shown in FIG. 5B or 5C or may be configured otherwise. In the example shown in FIG. 5B or 5C, the linear control edge 16Ca, 16Da defines the boundary with the first opening 15a, and the dimension of the stopper portion in the width direction N3, N4 decreases as the stopper portion extends in the direction N1 which is the blood movement direction. Therefore, when blood moves from the first opening 15a toward the second openings 15b, the blood is likely to move to the rear side, i.e. N1 side of the stopper portion 16C, 16D. As a result, regardless of the provision of the stopper portion 16C, 16D, the blood can properly move to the second openings 15b.

Figure 5D:
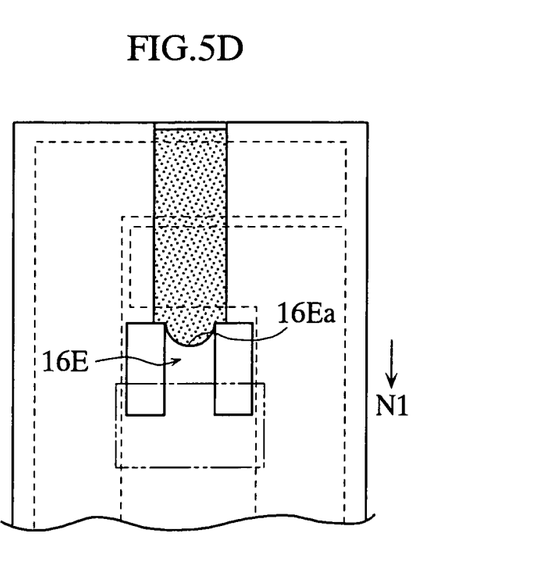

The stopper portion needs to have a configuration which can prevent the reagent solution from flowing into the second openings in forming the reagent portion. Therefore, instead of the above-described linear control edge, the stopper 16E may have a curved control edge dented in the direction of arrow N1 like the control edge 16Ea of shown in FIG. 5D. Although the stopper portion 16E shown in FIG. 5D is in the form of a peninsula, such a curved control edge is also applicable to a stopper portion in the form of an island separated from the insulating film.

The second opening may be configured as shown in FIGS. 6A-6D. Specifically, in the examples shown in FIGS. 6A and 6B, a single second opening 15Fb or 15Gb is provided. In the example shown in FIG. 6C, the second openings 15Hb are not offset from the first opening 15a in the direction of arrows N3, N4. In the example shown in FIG. 6D, each of the second openings 15Ib includes a narrow portion 15Ib' connected to the first opening 15a and a wide portion 15Ib" positioned downstream from the narrow portion 15Ib' (on the N1 side) in the blood movement direction. The second opening may be configured in various ways to have a configuration other than those shown in FIGS. 6A-6D.

The present invention is not limited to a glucose sensor configured to measure a glucose level in blood but also applicable to a glucose sensor for measuring a component in blood other than glucose (such as cholesterol or lactic acid) and also applicable to an analytical tool for analyzing a sample other than blood (such as urine or saliva), for example. Further, the present invention is not limited to an analytical tool which utilizes an electrode method but also applicable to an analytical tool configured to analyze a particular component in a sample by an optical method.

EXAMPLES

Hereinafter, it is proved that the glucose sensor according to the present invention can enhance the reproducibility of response current measurement and accurately measure a glucose level.

Inventive Example 1

Figure 6A:
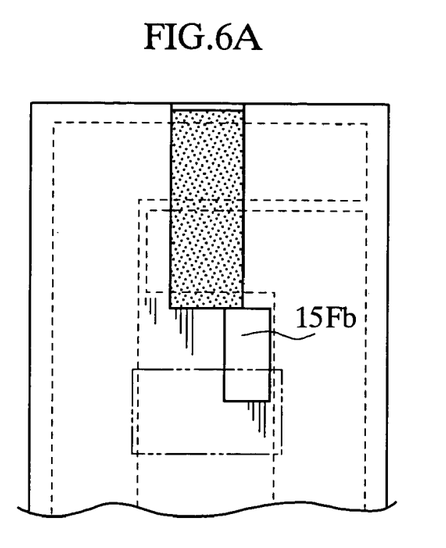
FIG. 6 includes plan views corresponding to FIG. 4, showing other examples of second opening of the glucose sensor.
Figure 6B:
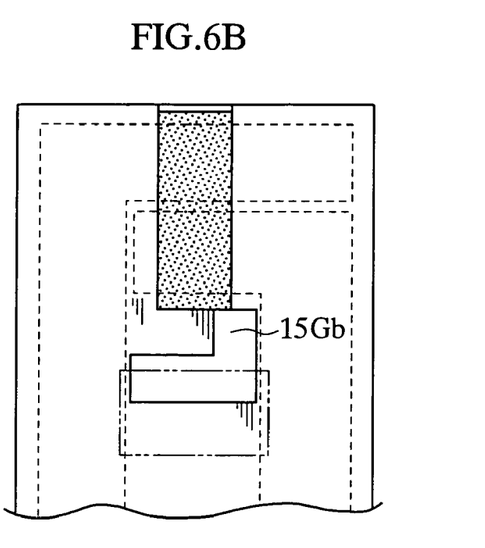
Figure 6C:
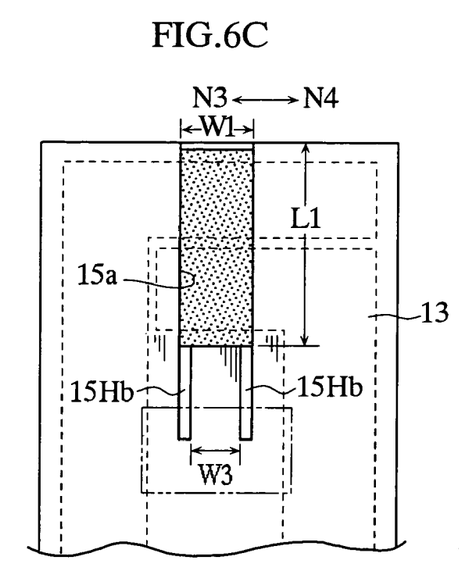
Figure 6D:
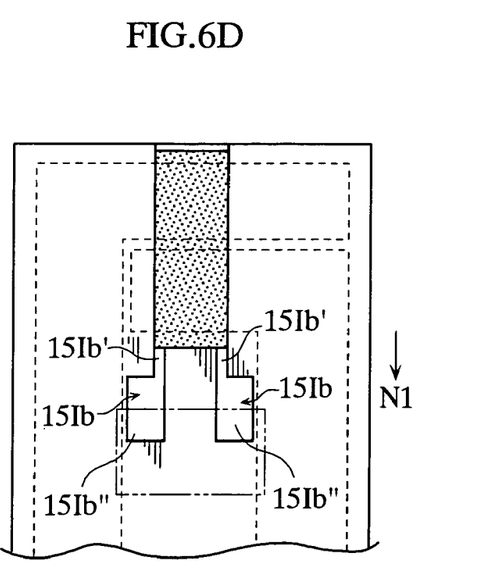

In this Inventive Example, use was made of a glucose sensor having a basic structure similar to that of the glucose sensor X shown in FIGS. 1 through 4 and second openings similar to the second openings 15Hb shown in FIG. 6C. Other conditions of the glucose sensor used in this Example are as follows.

The substrate 1 was made of PET (Tradename: "E-22" available from Toray Industries, Inc.) The working electrode 11 and the counter electrode 12 were formed to have a thickness of 10 μm by screen printing using carbon ink. The insulating film 13 was formed to have a thickness of 20 μm and a contact angle of 105 degrees by screen printing using water repellent resist ink. In the insulating film 13, the first opening 15a was formed to have a length L1 of 2.5 mm and a width W1 of 1.7 mm (See FIGS. 2 and 6C). In this Inventive Example 1, the stopper portion of the glucose sensor was formed to have a width W3 of 0.6 mm (See FIG. 6C). The reagent portion formed included [Ru (NH$_3$)$_6$]Cl$_3$ ("LM722" available from DOJINDO LABORATORIES) as electron mediator, and PQQGDH (Tradename: "PQQ-GDH" available from TOYOBO.CO., LTD.) as oxidoreductase. The electron mediator and the oxidoreductase were so included that respective concentrations upon dissolution due to the filling of the capillary 4 with blood become 4 vol % and 3 U, respectively. As the spacer 2, use was made of a double-sided tape (Tradename: "550PS5" available from SEKISUI CHEMICAL CO., LTD.). The cover was formed by using vinylon (Tradename: "vinylon sheet VF-LH" available from TOHCELLO CO., LTD.) The capillary 4 was formed to have a width W2 (See FIGS. 1 and 2) of 1.8 mm, a length L2 of 3.2 mm, and a height H2 (See FIG. 3) of 45 μm.

Figure 7A:
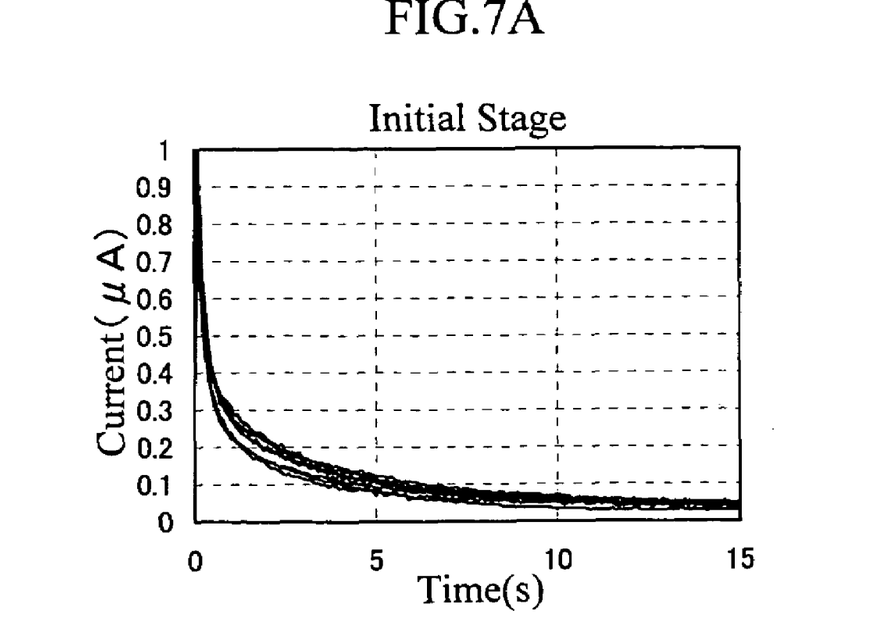
FIG. 7 includes graphs showing measurements of response current in Inventive Example 1.
Figure 7B:
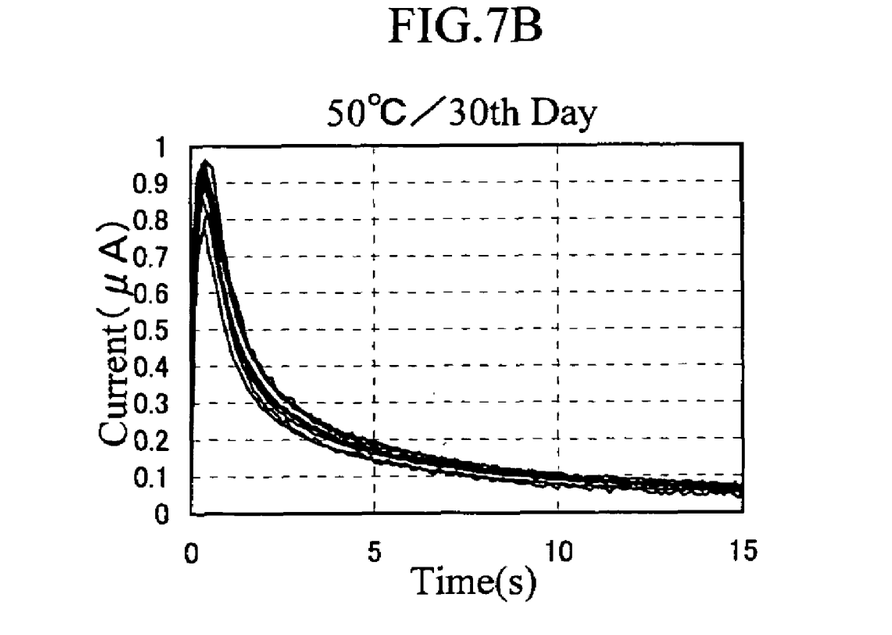

In this Inventive Example, the reproducibility was evaluated based on the time course of response current. The time course of response current was measured ten times by using whole blood having a glucose level of 400 mg/dL and a Hct of 42%. The application of voltage of 200 mV between the working electrode and the counter electrode was started five seconds after the start of the blood introduction, and the response current was measured over time, i.e. every 100 msec after the start of the voltage application. As the glucose sensor, two kinds of sensors were used, i.e. one immediately after the manufacturing and the other one stored for 30 days under the conditions of 50° C. and about 2% relative humidity after the manufacturing. FIGS. 7A and 7B show the measurement results of time course of the glucose sensor immediately after the manufacturing and the glucose sensor 30 days after the manufacturing, respectively.

Comparative Example 1

Figure 8A:
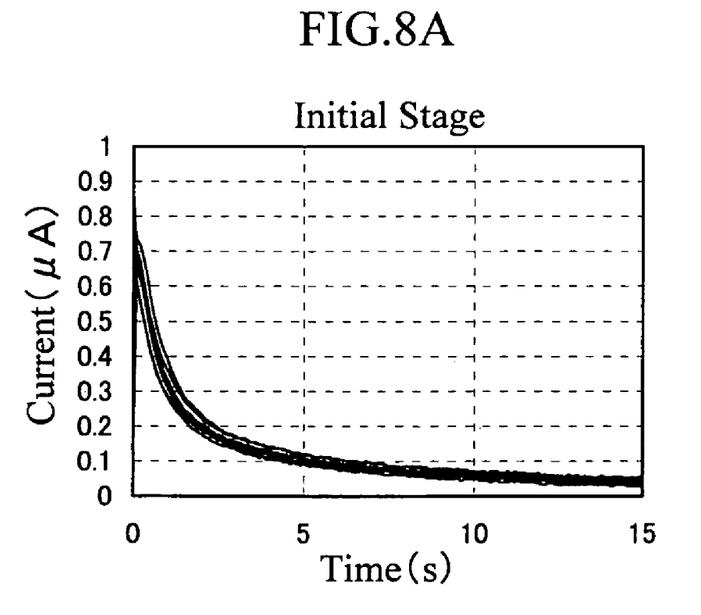
FIG. 8 includes graphs showing measurements of response current in Comparative Example 1.
Figure 8B:
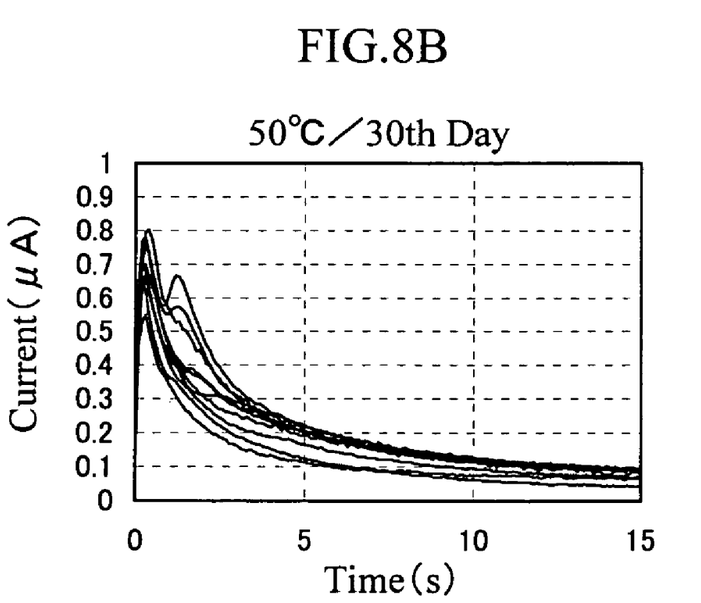

In this Comparative Example, the time course of response current was measured in the same way as in Inventive Example 1 except that a glucose sensor which did not include a second opening (FIGS. 9 through 11) was used. FIGS. 8A and 8B show the measurement results of time course of the glucose sensor immediately after the manufacturing and the glucose sensor 30 days after the manufacturing, respectively.

As will be understood from FIGS. 7A and 8A, with respect to the glucose sensors immediately after the manufacturing, disturbance of the time course is not found in both of the glucose sensor of Inventive Example 1 and that of Comparative Example 1. However, as will be understood from FIGS. 7B and 8B, with respect to the glucose sensors stored for 30 days, disturbance of the time course is not found in the glucose sensor of Inventive Example 1, whereas disturbance of the time course is found in the glucose sensor of Comparative Example 1. This result reveals that, by forming a second opening communicating with the first opening and a stopper portion like the glucose sensor of Inventive Example 1, a reagent portion can be properly formed in the first opening and the reproducibility of response current measurement can be enhanced. Moreover, the storage of the glucose sensor was performed under unfavorable conditions of 50° C. and about 2% relative humidity. This fact reveals that the glucose sensor of Inventive Example 1 can measure the response current with high reproducibility for a long period of time. Therefore, it is concluded that the glucose sensor of Inventive Example 1 can accurately measure the response current, and hence, measure the glucose level for a long period of time.

The invention claimed is:

1. An analytical tool with opening in insulating film, the tool comprising:
   a substrate;
   a flow path for moving a sample along the substrate;
   a reagent portion provided in the flow path;
   an insulating film covering the substrate and including a first opening for defining a region for forming the reagent portion and at least one additional opening positioned downstream from the first opening in a movement direction in which the sample moves, said at least one additional opening being connected to the first opening; and
   an island portion separated from the insulating film and including a control edge defining a downstream edge of the region for forming the reagent portion in the movement direction.

2. The analytical tool with opening in insulating film according to claim 1, wherein the flow path is configured to move the sample by capillary force.

3. The analytical tool with opening in insulating film according to claim 1, wherein the sample is blood.

4. The analytical tool with opening in insulating film according to claim 1, further comprising a first and a second electrodes provided at the substrate;
   wherein the insulating film covers the first and the second electrodes, with part of the first and the second electrodes exposed.

5. The analytical tool with opening in insulating film according to claim 1, wherein said at least one additional opening is connected to the first opening at a portion of the control edge adjoining in a direction which is perpendicular to the movement direction.

6. The analytical tool with opening in insulating film according to claim 1, wherein the control edge is in a form of a straight line extending in a direction which is perpendicular to the movement direction.

7. The analytical tool with opening in insulating film according to claim 6, wherein the first opening is rectangular; and
   wherein a dimension of the control edge in the perpendicular direction is set to 60 to 95% of a dimension of the first opening in the perpendicular direction.

8. The analytical tool with opening in insulating film according to claim 1, wherein the control edge is in a form of a curved line dented toward a downstream side in the movement direction.

9. The analytical tool with opening in insulating film according to claim 1, wherein the island portion has a width which decreases as the island portion extends downstream in the movement direction.

10. The analytical tool with opening in insulating film according to claim 9, wherein the island portion is triangular or semicircular.

11. An analytical tool with opening in insulating film, the tool comprising:
   a substrate;
   a flow path for moving a sample along the substrate;
   a reagent portion provided in the flow path; and
   an insulating film covering the substrate and including a first opening for defining a region for forming the reagent portion and a pair of additional openings positioned downstream from the first opening in a movement direction in which the sample moves, the additional openings being connected to the first opening;
   wherein the insulating film is formed with a peninsula portion including a control edge defining a downstream edge of the region for forming the reagent portion in the movement direction, the additional openings being arranged to adjoin the peninsula portion in a width direction,
   wherein each of the additional openings includes a narrow portion positioned relatively upstream in the movement direction and a wide portion positioned downstream from the narrow portion.

* * * * *